US00PP32968P2

(12) United States Plant Patent
Lüttmann et al.

(10) Patent No.: US PP32,968 P2
(45) Date of Patent: Apr. 13, 2021

(54) ***RHODODENDRON* PLANT NAMED 'MICROHIRS9'**

(50) Latin Name: ***Rhododendron* hybrid**
Varietal Denomination: Microhirs9

(71) Applicant: Inkarho GmbH, Bad Zwischenahn (DE)

(72) Inventors: Ralf Lüttmann, Bad Zwischenahn (DE); Walter Preil, Ammersbek (DE)

(73) Assignee: INKARHO GMBH, Bad Zwischenahn (DE)

( * ) Notice: Subject to any disclaimer, the term of this patent is extended or adjusted under 35 U.S.C. 154(b) by 0 days.

(21) Appl. No.: 16/873,813

(22) Filed: Jul. 14, 2020

(51) Int. Cl.
*A01H 5/02* (2018.01)
*A01H 6/36* (2018.01)

(52) U.S. Cl.
USPC ..... Plt./239
CPC ..... *A01H 6/364* (2018.05)

(58) Field of Classification Search
USPC ..... Plt./239
CPC ..... A01H 6/364; A01H 5/02
See application file for complete search history.

*Primary Examiner* — Keith O. Robinson
(74) *Attorney, Agent, or Firm* — Penny J Aguirre

(57) ABSTRACT

A new cultivar of hybrid *Rhododendron* plant named 'Microhirs9' that is characterized by its inflorescences that are conical in shape, its flowers that are pink in color with the upper surface of the center of the corolla lobes white in color, its compact plant habit, and its tolerance to alkaline soils.

2 Drawing Sheets

Botanical classification: *Rhododendron* hybrid.
Cultivar designation: 'Microhirs9'.

CROSS REFERENCE TO RELATED APPLICATIONS

This application is related to U.S. Plant Patent for a plant derived from the same breeding program that is entitled *Rhododendron* Plant Named 'Microhir3' (U.S. Plant Pat. No. 28,473). This application is related to a European plant breeders' rights application filed on Mar. 13, 2017, application No. 2017/0755 and a Canadian plant breeder's rights application filed on May 13, 2020, application No. 20-10194. There have been no offers for sale anywhere in the world prior to the effective filing date of this Application and no accessibility to one of ordinary skill in the art could have been derived from the printed plant breeder's rights documents.

BACKGROUND OF THE INVENTION

The present invention relates to a new and distinct cultivar of *Rhododendron* plant of hybrid origin, botanically known as *Rhododendron* hybrid 'Microhirs9' and will be referred to hereafter by its cultivar name, 'Microhirs9'. 'Microhirs9' is a new cultivar of deciduous *Rhododendron* grown for use as a landscape plant.

The new cultivar arose from a controlled breeding program with the objective of developing lime tolerant rootstock cultivars of *Rhododendron*. The new cultivar was derived from a cross made by the Inventors in 1997 in Edewecht, Germany between an unnamed and unpatented plant of *Rhododendron hirsutum* as the female parent, and an unnamed and unpatented plant of *Rhododendron micranthum*, as the male parent. The Inventors selected 'Microhirs9' as a single unique plant amongst the seedlings that resulted from the above cross in 2016 in Edewecht, Germany.

Asexual propagation of the new cultivar was first accomplished by softwood stem cuttings in Apen, Germany, in 2016 by the Inventors. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics 'Microhirs9'. These attributes in combination distinguish 'Microhirs9' as a new and distinct cultivar of *Rhododendron.*

1. 'Microhirs9' exhibits inflorescences that are conical in shape.
2. 'Microhirs9' exhibits flowers that are pink in color with the upper surface of the center of the corolla lobes white in color.
3. 'Microhirs9' exhibits a compact plant habit.
4. 'Microhirs9' exhibits tolerance to alkaline soils.

The female parent of 'Microhirs9' is similar to 'Microhirs9' in having flowers that are similar in size and corolla form and differs from 'Microhirs9' in flower color and in producing less flowers. The male parent of 'Microhirs9' is similar to 'Microhirs9' in having a similar number of flowers per inflorescence and differs from 'Microhirs9' in having flowers that are different in color and form. 'Microhirs9' can also be most closely compared to the *Rhododendron* cultivars 'Microhirs3' (U.S. Plant Pat. No. 28,473) and 'Intermedium'. 'Microhirs3' is similar to 'Microhirs9' in having a similar plant and growth habit. 'Microhirs3' differs from 'Microhirs9' in having inflorescences that are strongly dome-shaped and petal corolla lobes that are pink in color on the upper surface. 'Intermedium' is similar to 'Microhirs9' in corolla and leaf form but differs from 'Microhirs9' in the quantity of flowers and in flower color.

BRIEF DESCRIPTION OF THE DRAWINGS

The accompanying colored photographs were taken of a plant about 22 years in age (original Plant) of the new cultivar as grown outdoors in a garden in Rüsseldorf, Germany.

The photograph in FIG. 1 provides a side view of the overall plant habit of 'Microhirs9' in bloom.

Figure 1:
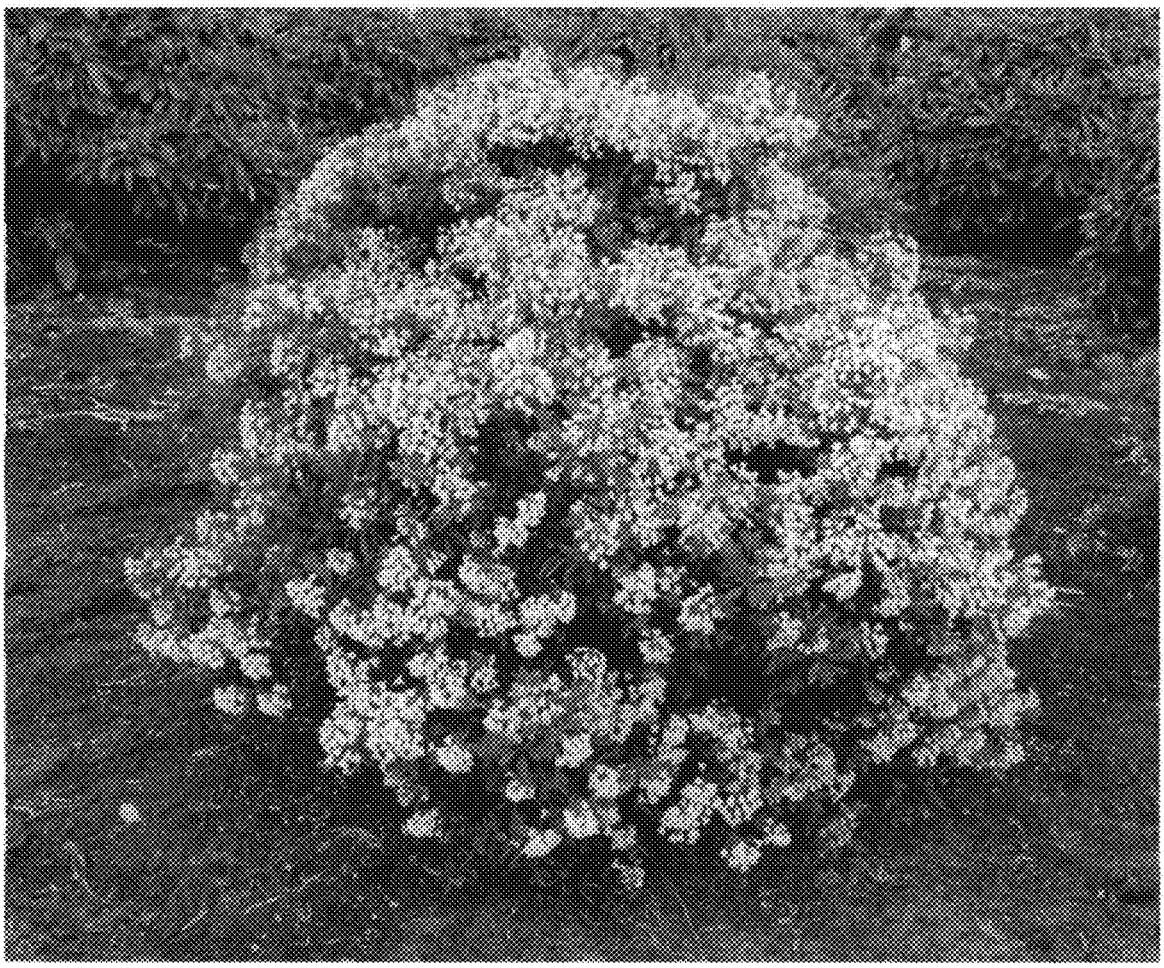
Figure 2:
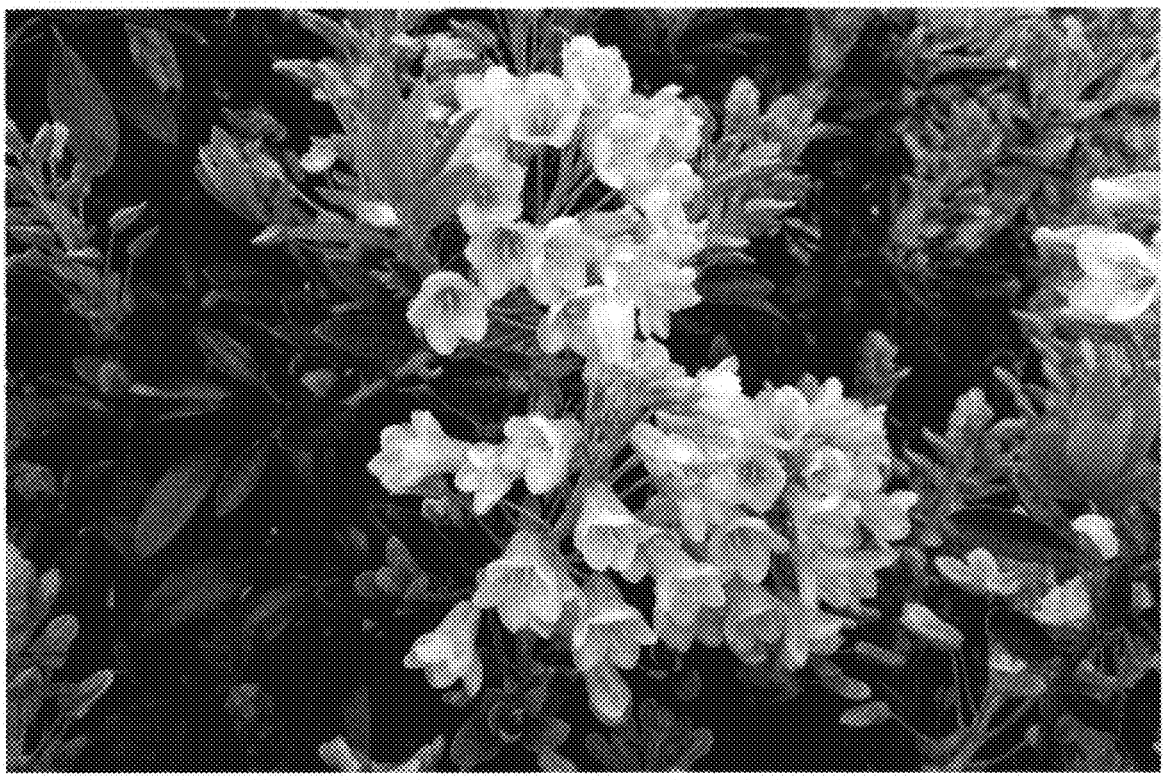

The photograph in FIG. 2 provides a close-up view of the inflorescences of 'Microhirs9'.

The colors in the photographs are as close as possible with the digital photography and printing techniques utilized and the color codes in the detailed botanical description accurately describe the new *Rhododendron*.

DETAILED BOTANICAL DESCRIPTION OF THE PLANT

The following is a detailed description of 15-month-old plants of the new cultivar as grown outdoors in 2-quart containers in Abbotsford, British Columbia, Canada. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General characteristics:

*Blooming period.*—End of May to middle of June in Northern Germany.

*Plant type.*—Evergreen shrub.

*Plant habit.*—Rounded, compact and densely branched.

*Height and spread.*—Average of 21 cm in height, 15 cm in diameter as a 1-year-old plant in a 2-quart container, reaches 1.2 m in height and width as a mature plant in the landscape.

*Cold hardiness.*—Plant is hardy to at least U.S.D.A. Zone 5b, it has not been confirmed if flower buds survive in Zone 5b or colder.

*Diseases and pests.*—No susceptibility or resistance to diseases or pests observed.

*Environmental tolerances.*—Observed to be lime tolerant.

*Root description.*—Fibrous and 200A in color.

*Propagation.*—Softwood stem cuttings.

*Growth rate.*—Moderate.

*Root development.*—6 weeks for root initiation and 1 year to produce a young plant from a rooted cutting.

Stem description:

*Shape.*—Round.

*Stem color.*—Young growth; 145A and 145B, mature growth; a blend of 152A and 178A, old wood; a blend of 200A, 197A, 184A.

*Stem size.*—Main stems; an average of 5 cm in length and 3 mm in width, lateral branches; an average of 4 cm in length and 2 mm in width.

*Stem surface.*—Young growth; very glossy, slightly rough to the touch, moderately covered in woolly pubescent hairs, up to 2 mm in length and 155A in color to matching stem surface, becoming smooth and glabrous in summer, mature wood; somewhat rough, dull and glabrous.

*Stem aspect.*—Held mainly vertical to slightly outward.

*Stem strength.*—Strong.

*Branching.*—Densely branched, an average of 4 main branches and 6 lateral branches per main branch.

Foliage description:

*Leaf shape.*—Elliptic to obovate.

*Leaf division.*—Simple.

*Leaf base.*—Cuneate.

*Leaf apex.*—Acute to obtuse.

*Leaf venation.*—Pinnate, inconspicuous, matches surface colors.

*Leaf margins.*—Entire and fringed with minute hairs; less than 0.5 mm in length and matches surface color.

*Leaf attachment.*—Petiolate.

*Leaf arrangement.*—Alternate, leaf clusters whorled.

*Leaf internode length.*—Ranges from 0.2 to 3.2 cm becoming progressively smaller from base to apex of shoot, 0.2 to 0.4 cm in whirl of foliage at shoot apex.

*Leaf orientation.*—Held mostly upright, some slightly downward.

*Leaf aspect.*—Whole leaf cupped upward with apex cupping downward.

*Leaf surface.*—Upper surface; smooth, glabrous, glossy with a thick texture, lower surface; smooth, dull, glabrous except prominent midrib with short cilia; <0.5 mm in length and similar in color to leaf surface.

*Leaf color.*—Young leaves upper surface; 143A, young lower surface; 144A, mature leaves upper surface; 147A, mature leaves lower surface; 147B.

*Leaf size.*—Average of 3 cm in length, 1 cm in width.

*Leaf quantity.*—An average of 25 leaves per lateral branch 15 cm length.

*Petioles.*—Average of 5 mm in length and 1 mm in diameter, color matches leaf upper surface colors, smooth and lightly pubescent surface.

Flower description:

*Inflorescence type.*—Umbellate raceme.

*Lastingness of inflorescence.*—Up to 3 weeks.

*Inflorescence size.*—Average of 5 cm in height and 4 cm in width.

*Inflorescence shape.*—Conical.

*Flower size.*—An average of 1 cm in depth and 1 cm in diameter.

*Flower fragrance.*—Lightly fragrant.

*Flower shape.*—Broad, tubular funnel.

*Flower number.*—Average of 24 per terminal shoot whorl.

*Flower aspect.*—Outward to slightly drooping.

*Flower bud.*—Average of 1 cm in length, 5 mm in diameter, a blend of 165A and 165B in color, oval to rounded in shape, matte surface, pointed tip.

*Flower attachment.*—Pedicellate.

*Petal number.*—5.

*Petal shape.*—Ovate to elliptic.

*Petal color.*—Young flowers before expanding; a blend of 71A and 144A, expanding flowers; (balloon stage), 71A and 71B, fully open upper and lower surface base and mid-section 67A and 73A, corolla lobe NN155C.

*Petal surface.*—Young upper and lower surface; densely covered with tiny pubescence matching surface colors, mature upper surface; glabrous and smooth to slightly rugose, lower surface; smooth, glabrous except for moderate pubescence along the midline.

*Petal margins.*—Entire, undulate.

*Petal apex.*—Acuminate to obtuse, often recurved.

*Petal base.*—60% fused.

*Petal size.*—An average of 2.5 cm in length and 5 mm in width.

*Sepal number.*—Whorled, 5.

*Sepal shape.*—Lanceolate.

*Sepal margin.*—Entire and fringed with hairs; 0.5 mm in length and 155A in color.

*Sepal size.*—Up to 1.5 cm in length and 5 mm in width.

*Sepal surface.*—Upper and lower surface glabrous and slightly glossy.

*Sepal apex.*—Acute.

*Sepal base.*—Petiolate, 3 mm in length, 1 mm in width, 145A in color.

*Sepal color.*—Young upper and lower surface 144A, mature upper and lower surface 147A.

*Bracts.*—Cup-shaped, surrounding individual flowers, 6 mm in length, 2 mm in width, flattened to pointed apex, acute base, matte surfaces, color; upper and lower surface a blend of 165A and 165B, self-cleaning as the inflorescence matures.

*Calyx.*—Shallow cup shape an average of 2 mm in length and 4 mm in diameter, 144B in color with individual sepals separated by rounded sinuses, densely pubescent, up to 1 mm in length and matches surface color.

*Pedicels.*—An average of 1 cm in length and 1 mm in diameter, 146C in color, lightly moderately pubescent surface; <0.5 mm in length, NN155A in color.

Reproductive organs:

*Gynoecium.*—1 Pistil, stigmas; round in shape, 140A in color, minute in size under 0.5 mm in diameter, style; average of 7 mm in length, 150D in color, ovary; 2 mm in length, superior, oblong in shape, 149A in color.

*Androecium.*—Stamens; average of 9, anthers; oblong to elliptical in shape, 2 mm in length and 0.5 mm in width, 163B in color; pollen; moderate in quantity, color 13A.

*Fruit/seeds.*—Not observed.

It is claimed:

1. A new and distinct cultivar of *Rhododendron* plant named 'Microhirs9' as herein illustrated and described.

* * * * *